(12) United States Patent
Berger

(10) Patent No.: US 9,592,071 B2
(45) Date of Patent: Mar. 14, 2017

(54) GROOVED DIRECTOR WITH INSTRUMENT GUIDE

(71) Applicant: J. Lee Berger, Franklin Lakes, NJ (US)

(72) Inventor: J. Lee Berger, Franklin Lakes, NJ (US)

( * ) Notice: Subject to any disclaimer, the term of this patent is extended or adjusted under 35 U.S.C. 154(b) by 104 days.

(21) Appl. No.: 14/524,850

(22) Filed: Oct. 27, 2014

(65) Prior Publication Data

US 2016/0113671 A1 Apr. 28, 2016

(51) Int. Cl.

| A61B 17/32 | (2006.01) |
|---|---|
| A61B 1/317 | (2006.01) |
| A61B 1/00 | (2006.01) |
| A61B 17/02 | (2006.01) |
| A61B 17/00 | (2006.01) |

(52) U.S. Cl.
CPC .. *A61B 17/320036* (2013.01); *A61B 1/00154* (2013.01); *A61B 1/317* (2013.01); *A61B 17/0218* (2013.01); *A61B 2017/0023* (2013.01); *A61B 2017/00424* (2013.01); *A61B 2017/00473* (2013.01); *A61B 2017/00557* (2013.01); *A61B 2017/00907* (2013.01); *A61B 2017/320048* (2013.01); *A61B 2017/320052* (2013.01)

(58) Field of Classification Search
CPC ............... A61B 1/00154; A61B 17/32; A61B 17/320016; A61B 17/320036; A61B 2017/0023; A61B 2017/00907; A61B 2017/1205; A61B 2017/320052; A61B 2017/320056

See application file for complete search history.

(56) References Cited

U.S. PATENT DOCUMENTS

| 2,164,926 A * | 7/1939 | Kleine ............ A61M 25/09025 |
| | | 604/170.02 |
| 3,537,452 A | 11/1970 | Wilks |
| 3,559,643 A | 2/1971 | Pannier, Jr. et al. |
| 3,592,193 A | 7/1971 | Higgins |
| 4,645,491 A * | 2/1987 | Evans ................. A61M 25/065 |
| | | 128/DIG. 18 |
| 4,655,214 A | 4/1987 | Linder |
| 5,011,478 A | 4/1991 | Cope |
| 5,029,573 A * | 7/1991 | Chow .................... A61B 1/317 |
| | | 600/104 |
| 5,179,963 A * | 1/1993 | Berger ............ A61B 17/32003 |
| | | 128/898 |

(Continued)

OTHER PUBLICATIONS

Chaise, F., Roger, B., "Pre- and post-operative CT scanning of the wrist in carpal tunnel syndrome", Rev Chir. Orthop., 72:297-302, 1986.

(Continued)

*Primary Examiner* — Ryan J Severson
(74) *Attorney, Agent, or Firm* — John S. Hale; Gipple & Hale

(57) ABSTRACT

A surgical grooved director including a fixed or removable handle with a tubular member having a lumen extending therethrough with an aperture at its proximal end and a blunt dissecting distal tip. An access window is formed through the wall of the tubular member in a distal portion of the instrument and is in communication with the lumen. An integral side rail is integrally mounted on the tubular member and defines a linear groove adapted to receive and allow slideable movement of a knife.

17 Claims, 6 Drawing Sheets

(56) References Cited

U.S. PATENT DOCUMENTS

| | | | | |
|---|---|---|---|---|
| 5,253,659 A * | 10/1993 | McNamara | A61B 17/32001 | 128/898 |
| 5,269,796 A * | 12/1993 | Miller | A61B 17/1659 | 606/167 |
| 5,273,024 A * | 12/1993 | Menon | A61B 17/3417 | 128/898 |
| 5,318,582 A * | 6/1994 | Chow | A61B 1/317 | 30/314 |
| 5,325,883 A * | 7/1994 | Orr | A61B 17/32003 | 128/898 |
| 5,346,503 A * | 9/1994 | Chow | A61B 1/317 | 30/314 |
| 5,356,419 A * | 10/1994 | Chow | A61B 1/317 | 30/314 |
| 5,400,768 A * | 3/1995 | McNamara | A61B 17/32001 | 600/104 |
| 5,429,117 A * | 7/1995 | McNamara | A61B 17/32001 | 600/104 |
| 5,545,136 A * | 8/1996 | Berger | A61M 29/00 | 128/898 |
| 5,620,446 A * | 4/1997 | McNamara | A61B 17/32003 | 128/898 |
| RE35,523 E * | 6/1997 | Berger | A61B 17/32003 | 128/898 |
| 5,730,749 A * | 3/1998 | Battenfield | A61B 17/32003 | 606/167 |
| 5,827,311 A * | 10/1998 | Berelsman | A61B 17/32003 | 30/294 |
| 5,908,431 A * | 6/1999 | Battenfield | A61B 17/32003 | 606/167 |
| 6,019,774 A * | 2/2000 | Weiss | A61B 17/32003 | 606/167 |
| 6,179,852 B1 * | 1/2001 | Strickland | A61B 17/32003 | 606/167 |
| 6,613,065 B2 * | 9/2003 | Lajtai | A61B 17/3417 | 606/190 |
| 6,706,069 B2 | 3/2004 | Berger | | |
| 7,780,690 B2 * | 8/2010 | Rehnke | A61B 1/313 | 600/104 |
| 8,216,185 B2 * | 7/2012 | Berger | A61B 17/32003 | 604/164.01 |
| 8,273,098 B2 * | 9/2012 | Strickland | A61B 17/32003 | 606/170 |
| 8,672,960 B2 * | 3/2014 | Briganti | A61B 17/32003 | 606/170 |
| 8,827,893 B2 * | 9/2014 | Mirza | A61B 1/018 | 600/114 |
| 8,852,191 B2 * | 10/2014 | Bertram, III | A61B 17/32001 | 606/102 |
| 2002/0123764 A1 * | 9/2002 | Lajtai | A61B 17/3417 | 606/190 |
| 2004/0054378 A1 * | 3/2004 | Yang | A61B 17/32003 | 606/191 |
| 2007/0288043 A1 * | 12/2007 | Rehnke | A61B 1/313 | 606/170 |
| 2008/0109021 A1 * | 5/2008 | Medoff | A61B 17/32003 | 606/167 |
| 2009/0048620 A1 * | 2/2009 | Weiss | A61B 17/32003 | 606/167 |
| 2010/0100046 A1 * | 4/2010 | Berger | A61B 17/32003 | 604/164.12 |
| 2010/0100114 A1 * | 4/2010 | Berger | A61B 17/0218 | 606/191 |
| 2010/0228085 A1 * | 9/2010 | Mirza | A61B 1/018 | 600/106 |
| 2012/0016397 A1 * | 1/2012 | Briganti | A61B 17/32003 | 606/167 |
| 2012/0016398 A1 * | 1/2012 | Strickland | A61B 17/32003 | 606/170 |
| 2012/0323245 A1 * | 12/2012 | Bertram, III | A61B 17/32003 | 606/88 |
| 2013/0144318 A1 * | 6/2013 | Dinis Carmo | A61B 17/32001 | 606/170 |
| 2014/0088354 A1 * | 3/2014 | Mirza | A61B 1/018 | 600/106 |
| 2014/0343357 A1 * | 11/2014 | Mirza | A61B 1/018 | 600/104 |
| 2014/0371526 A1 * | 12/2014 | Mirza | A61B 1/018 | 600/104 |
| 2016/0113671 A1 * | 4/2016 | Berger | A61B 17/32003 | 600/104 |

OTHER PUBLICATIONS

Gartsman, Gary, M., Kovach, John, C., et al., "Carpal arch alteration after carpal tunnel release", J. Hand Surg. (AM.),11-A372-374, May 1986.

Jakab, Emery, Ganos, Doreen, et al., "Carpal tunnel release: Post-operative care", Handchirurgie, 20:39-40, Jan. 1988.

Kulick, Michael, I., D.D.S., M.D., et al., "Long-term analysis of patients having surgical treatment of carpal tunnel syndrome", Jour. of Hand Surg; 11A (1):59-66, 1986.

Nancollas, Michael P., "Symptoms may return after carpal tunnel surgery", JAMA; vol. 265, No. 15, p. 1922, Apr. 17, 1991.

\* cited by examiner

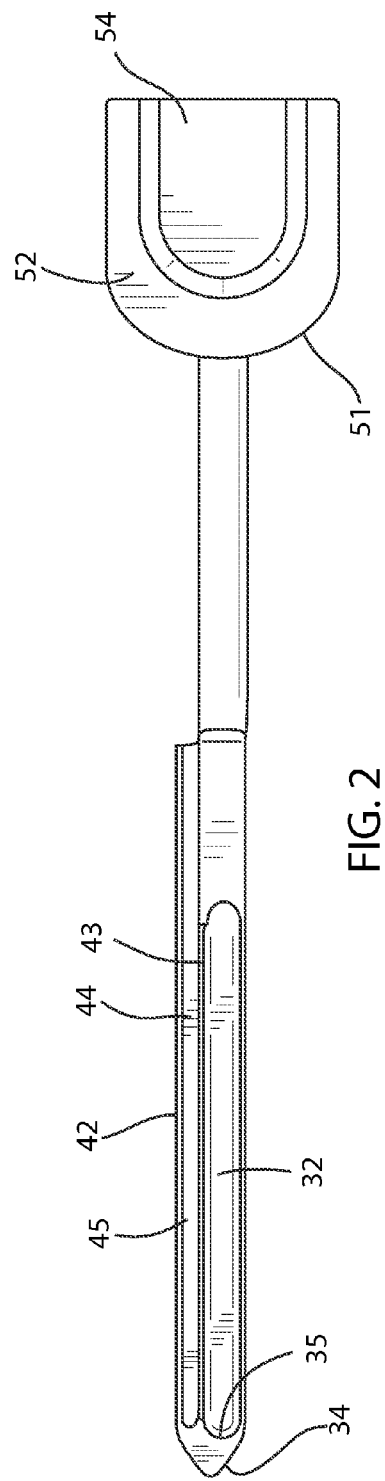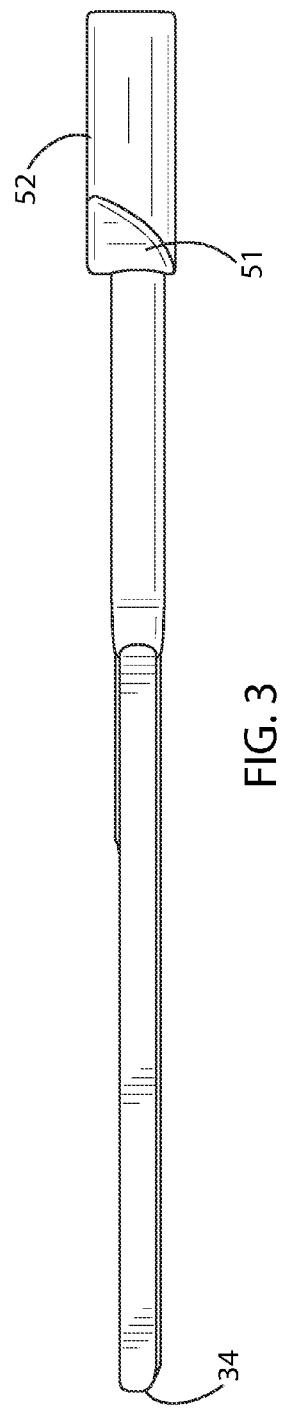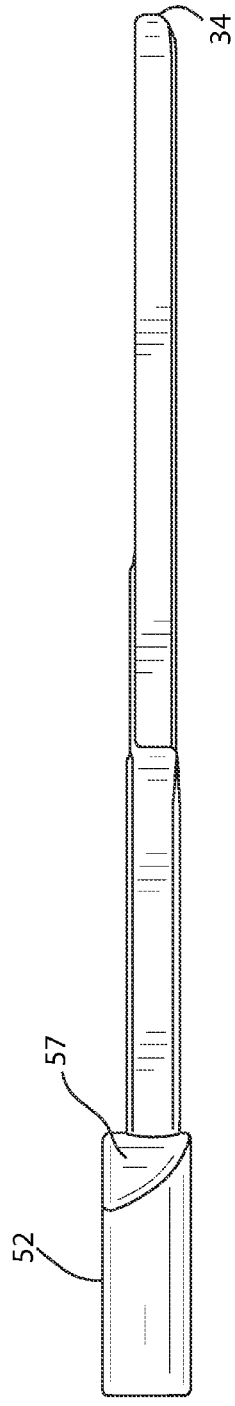

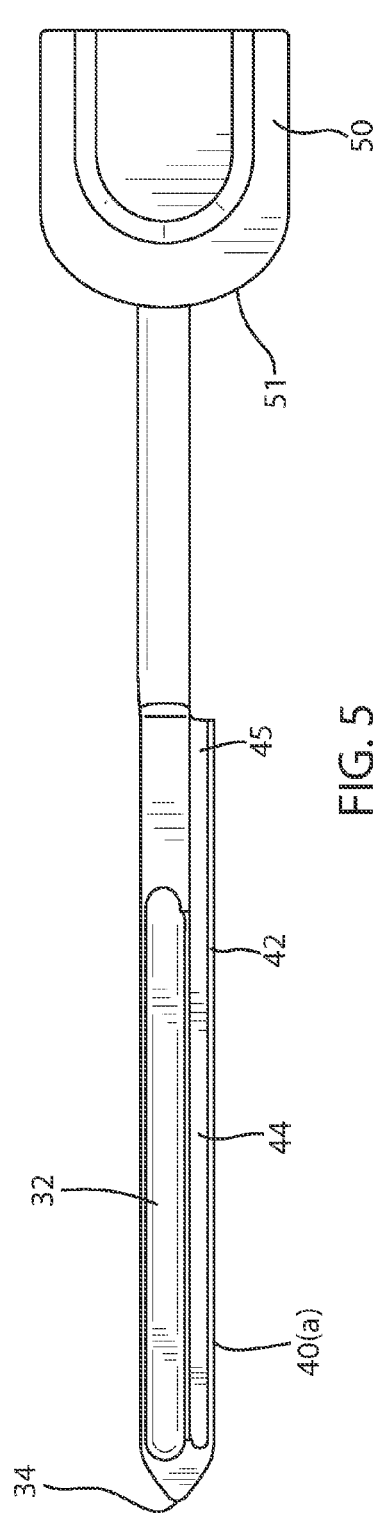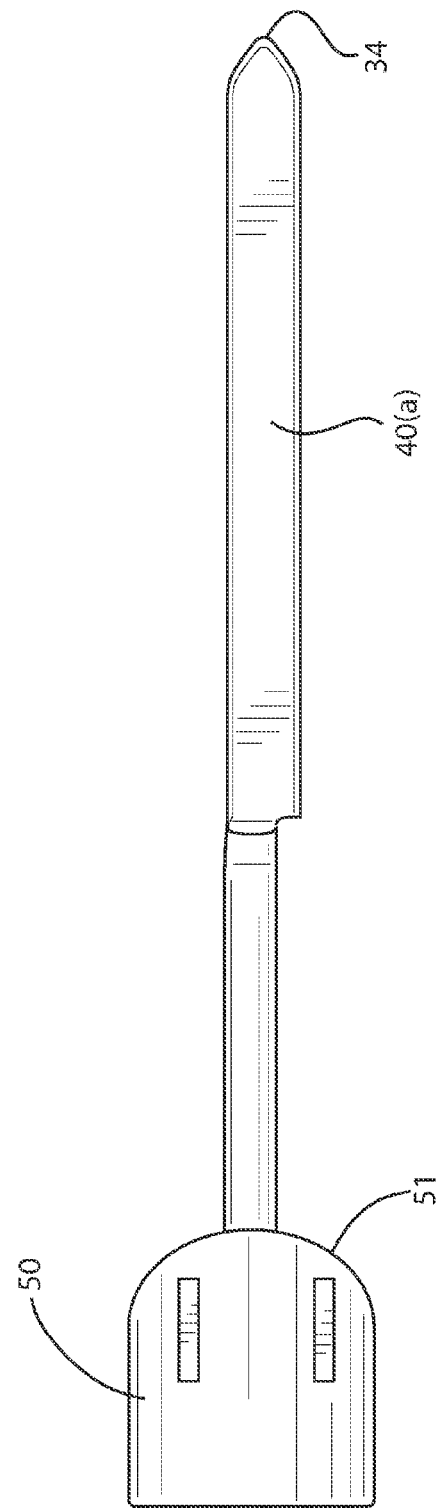

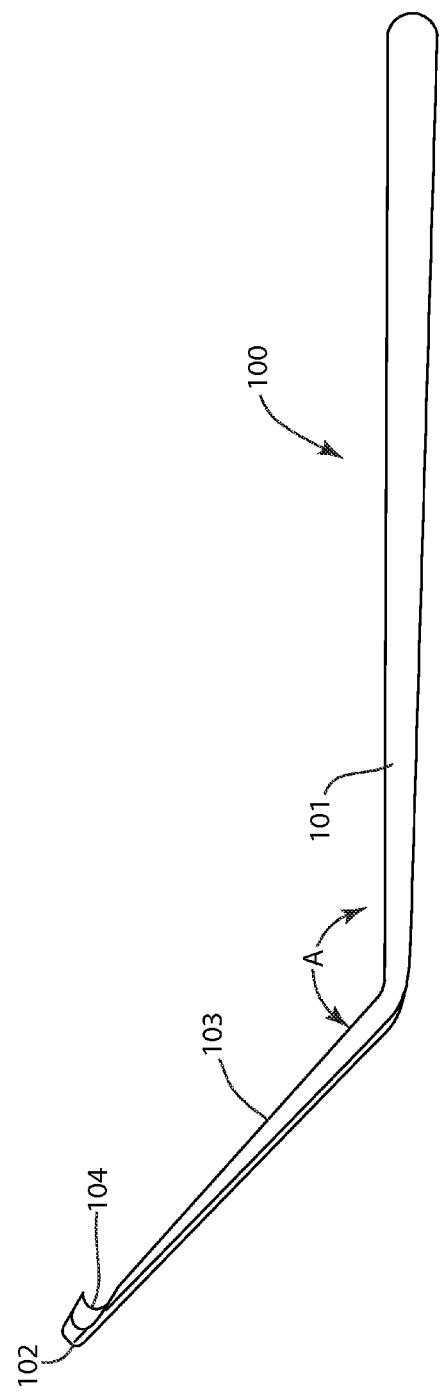
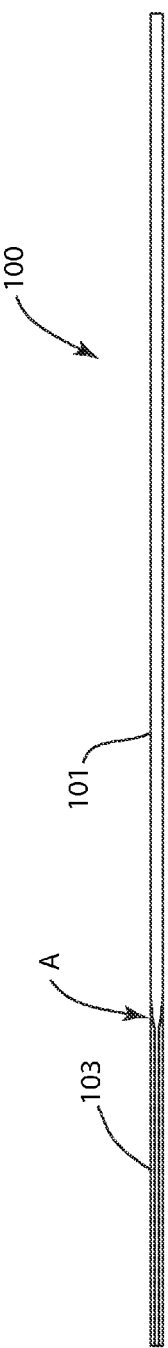
FIG. 8
FIG. 9
FIG. 10

GROOVED DIRECTOR WITH INSTRUMENT GUIDE

RELATED APPLICATIONS

This is a continuation-in-part of U.S. patent application Ser. No. 12/289,075 filed on Oct. 20, 2008.

STATEMENT REGARDING FEDERALLY SPONSORED RESEARCH OR DEVELOPMENT

None

REFERENCE TO SEQUENCE LISTING, A TABLE OR A COMPUTER PROGRAM LISTING COMPACT DISC APPENDIX

None.

BACKGROUND OF THE INVENTION

1. Field of Invention

The present invention relates to a cannulated tubular surgical grooved director with an integral side instrument guide configured to guide surgical instruments. The device may be used as a conventional tissue expander for orthopaedic or general surgery, and is particularly suited for use in accessing the carpal tunnel region during carpal tunnel syndrome procedures.

2. Background of the Invention

The use of a cannula, sheath, or director to guide or ease insertion of surgical instruments or to facilitate access to a surgical field is well known. With particular reference to the carpal tunnel syndrome, these devices are commonly used to facilitate the introduction of a balloon catheter that is serially inflated and deflated in the carpal canal during surgery to alleviate entrapment of the nerve.

Carpal tunnel syndrome is a common painful condition of the hand characterized by a decrease in median nerve sensibility with paresthesias of the fingers. It is the most common nerve entrapment syndrome of the upper extremity and results from compression of the median nerve in the carpal tunnel and its symptoms include nocturnal pain, clumsiness, and weakness of grasp or pinch.

The carpal canal is the area in the wrist and palm of the hand formed by the U-shaped cluster of bones of the carpus that forms the rigid hard floor and the two sides of the tunnel. Within the confines of this space are the median nerve, and the extrinsic flexor tendons of the thumb and fingers with their surrounding synovial membranes of the radial and ulna brusae. The roof of the tunnel is formed by the transverse carpal ligament on the palmar surface of the carpal bones. The ligament is attached medially to the pisiform and the hamulus of the hamate, and laterally to the tuberosity of the scaphoid and the medial part of the palmar surface and ridge of the trapezium. The proximal border of the ligament is partially merged to the distal border of the palmar carpal ligament, a more superficial structure separated from the transverse carpal ligament by the ulnar artery and nerve. The transverse carpal ligament is attached to the palmar aponeurosis, which lies superficial, and contributes crossed oblique fibers to the deep surface of the aponeurosis.

Any condition that diminishes the size of the carpal tunnel can precipitate the carpal tunnel syndrome. Repetitive wrist and hand motions can cause thickening and hypertrophy of the transverse carpal ligament. Proliferation of synovium from normal wear and tear of daily activities can cause compression of the median nerve within the closed confines of the carpal tunnel. Furthermore, systemic conditions such as pregnancy, obesity, diabetes mellitus, thyroid dysfunction, or chronic renal failure can initiate the syndrome. Generally, the syndrome occurs most often in patients between the ages of 30 and 60 years and is five times more frequent in women than in men.

Failure to correct the condition in a timely manner ultimately results in irreversible muscle damage, as indicated by denervation potentials.

Historically, carpal tunnel syndrome has been treated nonsurgically by splinting of the affected hand and wrist, oral anti-inflammatory medication, and local steroid injection. Where nonsurgical methods are unsuccessful, surgical intervention is necessary.

Open surgical decompression of the carpal tunnel by division of the transverse carpal ligament was first described in 1930 by Learmonth. Open surgical procedures generally entail a curved longitudinal incision to the ulnar side and parallel to the thenar crease. Another open procedure angles the incision towards the ulnar aspect of the wrist which helps to avoid cutting the palmar sensory cutaneous branch of the median nerve. After dissection of the skin and subcutaneous tissue, the transverse carpal ligament is identified and divided along its ulnar border to avoid and to prevent injury to the median nerve or its recurrent branch.

Open surgical decompression of the median nerve is not without risks and complications. Long term analysis of patients who have undergone surgical treatment for carpal tunnel syndrome have shown a failure rate as high as 19% (Kulick, Michael, I., D.D.S., M.D., et al.; Jour of Hand Surg; 11A (1):59-66. 1986). Thirty percent of all patients in one study were rated with poor after fair result at an average of 5.5 years follow-up; "57% of the patients in the study complained of return of some preoperative symptoms, most commonly pain, beginning an average of 2 years after surgery." (Nancollas, Michael P.; Symptoms may return after carpal tunnel surgery; JAMA; Vol 265, No 15, p 1922, Apr. 17, 1991.) Complications include continued pain and or numbness, hypersensitive scar, loss of grip strength, joint stiffness, adherence of flexor tendons, neuroma, injury to the median nerve or its motor branch or digital nerve injury, damage to the palmar cutaneous nerve, vascular injury, palmar hematoma, infection, and possible reflex sympathetic dystrophy.

A retrospective analysis of 40 cases of reoperation for carpal tunnel syndrome found adhesions and fibrosis around the median nerve in the carpal canal in 36 cases. (Wadstroem, J., Nigst, H.; Reoperation for carpal tunnel syndrome: a retrospective analysis of 40 cases; Ann. Chir. Main; 5:54-58, 986.)

Hand weakness with loss of grip strength can also be a problem. Carpal tunnel release produces an average widening of the transverse carpal arch of 2.7 mm. There is a direct relationship between widening of the carpal canal and decreased grip strength. The average decrease in grip strength is 12%. (Gartsman, Gary, M., Kovach, John, C., et al.; Carpal arch alteration after carpal tunnel release; J. Hand Surg. (AM.) 11-A:372-374, May, 1986.) Computerized tomographic (CT) studies of the carpal tunnel after transection of the transverse carpal ligament have shown that if the flexor retinaculum is not intact, the flexor tendons will bowstring palmarly when the wrist and fingers are flexed together, causing weakness of grip. Some authors have recommended the use of a firm postoperative compression dressing immobilizing the wrist in slight dorsal extension for 3 weeks to prevent prolapse of the flexor tendons. (Jessurun, W, Hillen, B, et al.; Carpal tunnel release: Postoperative care: Handchirurgie 20:39-40, January, 1988.)

Because of the concern over widening of the carpal arch with subsequent decrease in grip strength, following standard carpal tunnel release, Jakab and associates devised a technique employing reconstruction of the transverse carpal ligament. (Jakab, Emery, Ganos, Doreen, et al.; Carpal tunnel release: Postoperative care: Handchirurgie 20:39-40, January, 1988.) These authors learned that by reconstructing the transverse carpal ligament, the transverse carpal arch was stabilized affording protection to the median nerve and preventing potential bow-stringing of the flexor tendons. By repairing the transverse carpal ligament the normal relationship of the carpal canal and its contents was restored and maintained.

Pre and post-operative CT scanning of the wrist in carpal tunnel syndrome has been performed and has shown that postoperative decompression results in the regeneration of a much more flexible ligament, which allows the contents of the tunnel, to expand anteriorly. The divided transverse carpal ligament heals in a stretched or arched position allowing more room for the median nerve and flexor tendons. (Chaise, F., Roger, B.; Pre- and post-operative CT scanning of the wrist in carpal tunnel syndrome; Rev Chir. Orthop.; 72:297-302' 1986.)

In recent years endoscopic techniques have been utilized to incise and divide the transverse carpal ligament. Attempts have been made to decrease the size of the surgical incision with the benefit of decreasing postoperative complications because hand strength returns quickly and the hand is less tender.

Refinements of endoscopic release of the carpal ligament are evolving but complications with this procedure have been reported The complications include neuropraxia of the median and or ulnar nerve, digital nerve laceration, laceration of palmar vessels, laceration of flexor tendons, neuropraxia or laceration of the palmar cutaneous branch of the median nerve, palmar hematoma, adhesions of tendons, perineural fibrosis, bowstringing of flexor tendons with loss of grip strength, incomplete transsection of the carpal ligament with recurrence of symptoms and hypertrophic scar.

U.S. Pat. No. 5,179,963 issued Jan. 19, 1993 to the present inventor solves these aforementioned complications and employs a balloon catheter device with a separate nerve protector inserter and pressure gauge monitor. The balloon catheter is inserted percutaneously and is utilized to dilate and expand the transverse carpal ligament, through serial applications of fluid pressure while it is moved along the carpal tunnel, thereby increasing the diameter of the carpal tunnel, relieving compression of the median nerve and alleviating the symptoms of carpal tunnel syndrome. Percutaneous dilatation of the transverse carpal ligament increases the spatial diameter of the carpal tunnel, thereby relieving pressure on the median nerve in the hand and wrist without the surgical and treatment problems previously discussed.

U.S. Pat. No. 5,545,136 issued Aug. 13, 1996, also issued to the present inventor, discloses a surgical instrument used in the treatment of carpal tunnel syndrome having a rigid tubular member with lumen through which a balloon carpal tunnel plasty procedure may be undertaken. The balloon expands through an aperture in the radial wall of the tubular member and the tubular member includes a rigid, solid rounded tip to ease insertion of the apparatus into the carpal tunnel. Other instruments are then used in conjunction with the instrument to perform the surgery.

U.S. Pat. No. 6,706,069 issued Mar. 16, 2004, also issued to the present inventor, is directed toward a grooved director with a built in balloon which is inflated by a pump to a predetermined pressure to expand the walls of a collapsed vertebra. The device is inserted into the body of the compressed vertebra and the grooved director is positioned and aimed in a direction under the compressed superior end plate of the vertebral body. The balloon inside of the grooved director is inflated and the force and direction of balloon inflation restores the height of the fractured vertebrae. The balloon is deflated and the grooved director is circumferentially rotated while intermittently inflating and deflating the balloon to create a symmetrical space within the center of the vertebral body. The balloon is deflated and the grooved director device with balloon is removed leaving a rebuilt vertebra which may be filled with a biocompatible material.

U.S. Pat. No. 4,655,214 issued Apr. 7, 1987 shows a soft inflatable sheath having a closed rounded distal tip that is inserted through a catheter and inflated adjacent the distal tip of the catheter prior to intubation. The proximal end of the sheath is sealed to maintain it in an expanded condition when the catheter is being intubated. Following intubation the cylindrical sheath is deflated and withdrawn. U.S. Pat. No. 4,645,491 issued Feb. 24, 1987 shows a catheter placement apparatus used in inserting a catheter to a preferred depth. The device comprises a surgical needle provided with a thin-walled transparent polytetrafluoroethylene tube which is heat shrunk over the stem portion of the needle to form a longitudinal window allowing a catheter inserted in the needle to be viewed. The catheter has a colored patch of the same length as the window and a series of spaced circular bands of differing colors allowing the position of the catheter to be accurately located by lining the colored patch with the window and advancing the catheter until at least one band appears in the window. The color and distance of the band nearest to the surface of the patient's skin are used to determine the position of the catheter. The surgical needle is withdrawn by sliding it along and off the catheter. U.S. Pat. No. 2,164,926 issued Jul. 4, 1939 shows a catheter stylet with an eye or aperture positioned on an opposite lateral wall behind the tip. U.S. Pat. No. 3,537,452 issued Nov. 3, 1970 shows a needle guard and beveled cutter for use with intravenous catheterization units. The device has a tubular body with a flat base and a longitudinally slotted top. The diameter of the tube is greater than the diameter of the needle contained therein. U.S. Pat. No. 3,592,193 issued Jul. 13, 1971 shows a removable needle guide used with a flexible catheter tube in withdrawing or introducing fluids relative to a body. The hollow tubular needle guide has a sharpened needle portion provided at its proximal end for puncturing the skin, tissues and veins of the body where the needle is inserted. At its distal end, the guide has winged handles which provide controlled insertion and removal from the body with subsequent attachment from a flexible catheter tube. U.S. Pat. No. 5,011,478 issued Apr. 30, 1991 shows an introducer set including a sheath and dilator formed with a smooth external shape. The distal end of the sheath is embedded in the dilator and formed in angle oblique to the longitudinal access of the introducer set. U.S. Pat. No. 3,559,643 issued Feb. 2, 1971 shows a catheter placement unit for insertion of a catheter into a body lumen through an incised opening in the lumen wall. The unit includes a longitudinally slit sheath having a catheter therein and an advancer connected to one end of the catheter, initially in axial alignment with the sheath to close the end of the sheath.

There is presently a need, however, for an orthopedic and general surgical director instrument that combines various features of multiple instruments. When carpal tunnel release procedures are undertaken as described above, an instrument similar to known elevator devices is needed to extend the reach of the surgeon into the confines of the operating field and facilitate elevation, retraction, cutting and/or manipulation of the tissues therein. Particularly regarding the surgical carpal tunnel intervention described supra, the instrument of the present invention is uniquely combined with a balloon catheter mounted within its hollow interior so that its balloon may be deployed from a protected window in the distal portion of the instrument and a surgical knife may be deployed via the side guide rail to cut tissue as needed.

SUMMARY OF THE INVENTION

The present invention is a multi-functional surgical tool intended for use as a conventional tissue expander or instrument guide for orthopaedic or general surgery. The instrument is a generally rigid, rod-like tubular member which is open at its distal end allowing a balloon catheter to be inflated or deflated as desired by the user against tissue and a gripping handle mounted to its proximal end. The instrument has a grooved side rail integral and adjacent the tubular member which is used to guide a surgical knife to dissect, elevate, and retract tissues within the surgical field.

The instrument is ideally suited for hand and wrist surgery, particularly with regard to endoscopic and balloon assisted carpal tunnel release. Additional surgical uses will be immediately obvious to those skilled in the art and include use in a variety of elbow, shoulder, hip, knee, ankle, and foot procedures.

In an alternative embodiment, the closed distal tip of the tissue expander described above can be optically clear and refractive, and the tubular member is sized so that its' lumen can accommodate an arthroscope or endoscope. The aforementioned scope may then be inserted whereby the visual field viewed through the closed distal tip is modified by the optical properties of the tip. The interior (i.e., facing the lumen of the present invention) or exterior surfaces of the tip may be ground with refractive indeces that, for example, permit wide angle viewing and illumination through the distal tip. Alternatively, the tip may be ground to provide a highly directed, magnified view, or the tip may simply be non-refractive and serve to protect the tip of an arthroscope or endoscope inserted therein.

In yet another alternative embodiment, the medical instrument described above may receive or incorporate inflation means, for example gas or fluid delivery pumps such as syringes generally known to those in the field such that a balloon may then be pressurized when the instrument is inserted in the tissue to elevate the tissue away from the instrument.

In still another alternative embodiment of the present invention, the handle is removable from the instrument.

It is an object of this invention to provide a multi-functional surgical instrument.

It is another object of this invention to provide a combination tissue elevator and balloon treating instrument with associated cutting tools for orthopedic and general surgery.

It is further object of the this invention to provide instrument which allows a cutting knife to be guided along both sides of the instrument to provide exact placement of the knife on the area of the tissue to be cut.

It is still another object of this invention to provide a multi-functional surgical instrument in multiple sizes to accommodate various surgical procedures and instrumentation.

It is an object of this invention to provide an inexpensive to manufacture a biologically inert and autoclavable surgical instrument.

It is yet another object of this invention to provide an inexpensive and disposable surgical instrument.

The invention will be better understood and objects other than those set forth above will become apparent when consideration is given to the following detailed description thereof. Such description makes reference to the annexed drawings wherein.

BRIEF DESCRIPTION OF THE DRAWINGS

FIG. 2 is an enlarged top plan view of the grooved director instrument shown in FIG. 1 without the balloon catheter and pump;

FIG. 3 is a side elevational view of the grooved director with integral side rail shown in FIG. 2;

FIG. 4 is an opposite side elevational view of the grooved director with integral side rail shown in FIG. 2;

FIG. 5 is a top plan view of the grooved director with integral side rail secured to the opposite side of the grooved director from that that shown FIGS. 1-4;

FIG. 6 is a bottom plan view of the grooved director with integral side rail shown in FIG. 5;

FIG. 8 is an enlarged side elevational view of the surgical knife shown in FIG. 7 removed from the grooved director with integral side guide rail;

FIG. 9 is a top plan view of the surgical knife shown in FIG. 8

FIG. 10 is a bottom plan view of the surgical knife shown in FIG. 8; and

Figure 1:
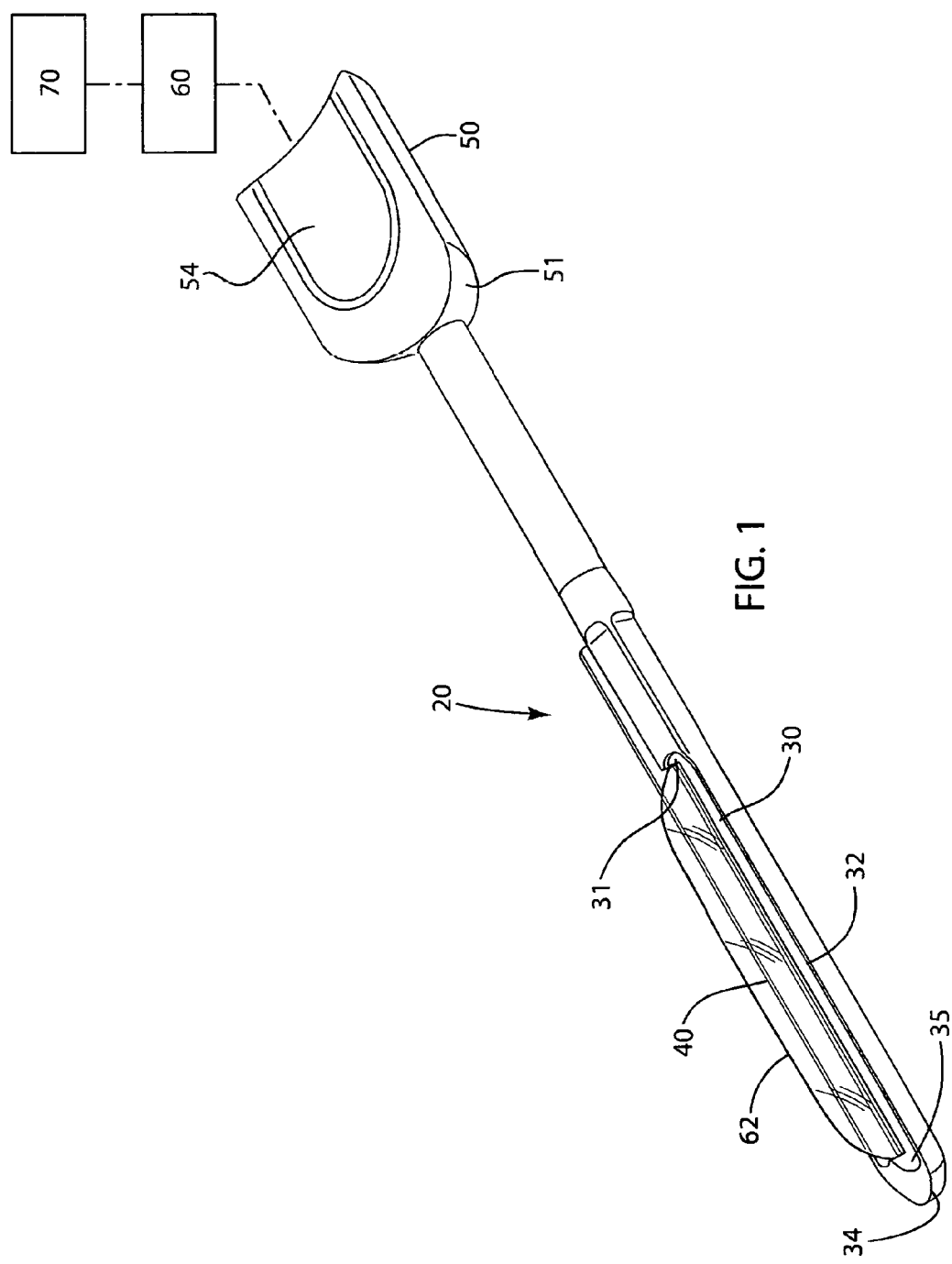
FIG. 1 is a perspective view of the grooved director instrument with an integral side guide rail with schematic blocks showing the relationship of the instrument when a balloon catheter and pump are used with the invention.
Figure 7:
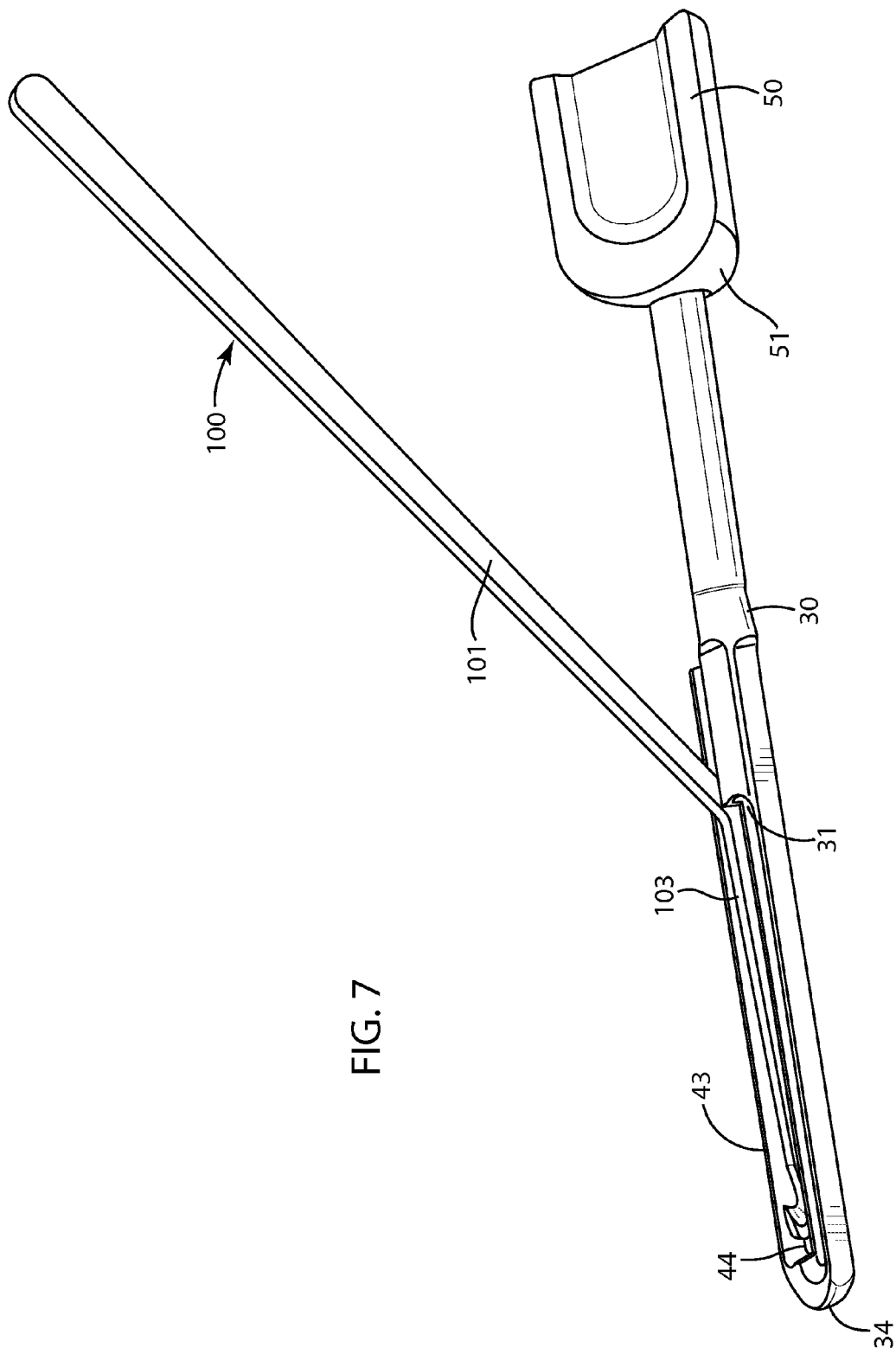
FIG. 7 is a perspective view of the grooved director with integral side rail shown in FIG. 1 with a surgical knife mounted in the guide groove of the integral side guide rail.
Figure 11:
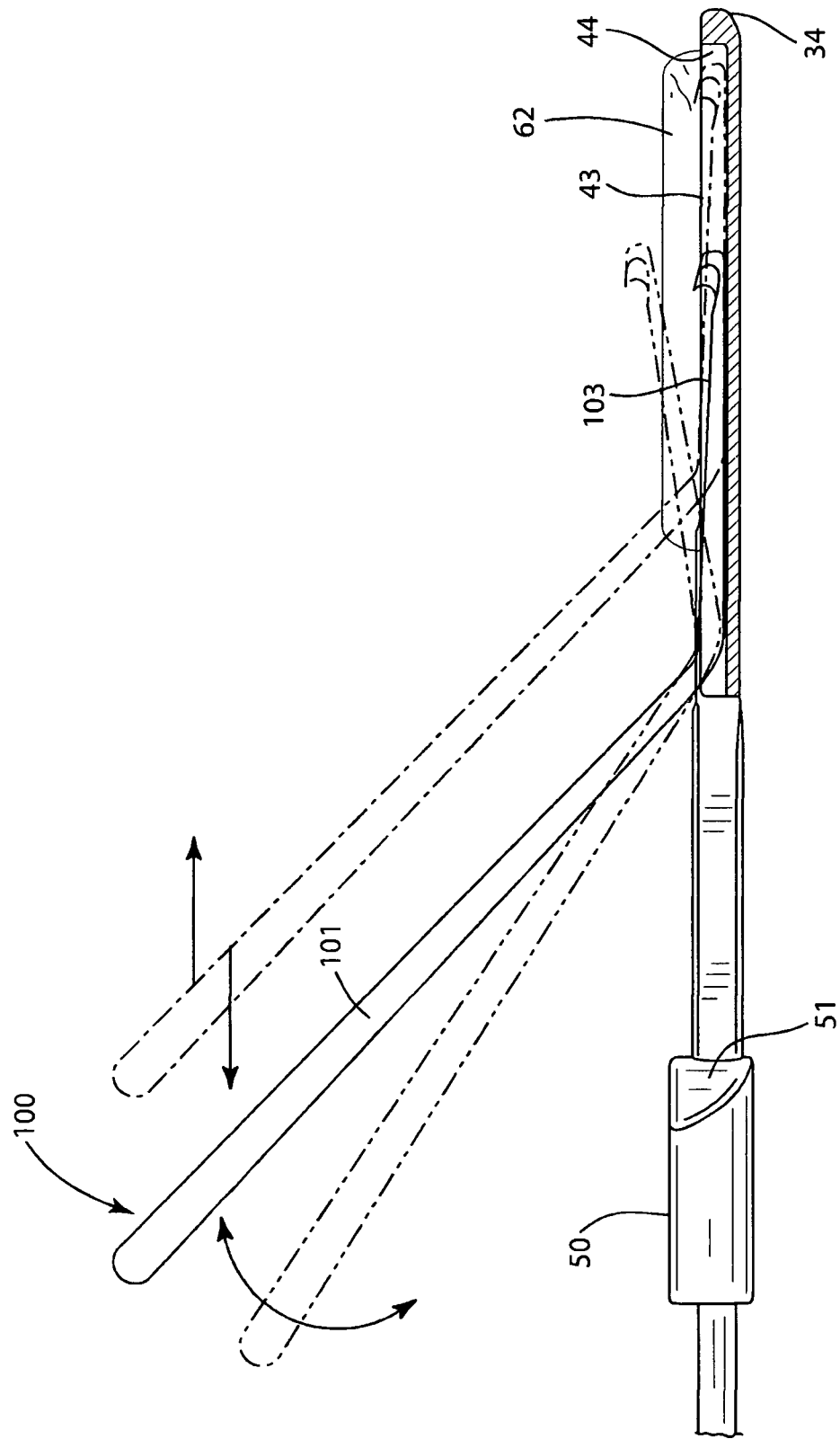
FIG. 11 shows the surgical knife in selected real and phantom positions mounted in the guide groove of the integral side guide rail.

These and other objects, advantages, and novel features of the present invention will become apparent when considered with the teachings contained in the detailed disclosure along with the accompanying drawings.

DESCRIPTION OF THE INVENTION

The best mode and preferred embodiment of the present invention is shown in FIGS. 1 through 11. While the invention is described in connection with certain preferred embodiments, it is not intended that the present invention be so limited. On the contrary, it is intended to cover all alternatives, modifications, and equivalent arrangements as may be included within the spirit and scope of the invention as defined by the appended claims.

The invention is a cannulated, and generally tubular instrument having a stepped cut out opening at its distal end with an integral side guide rail configured to guide a surgical knife to a selected surgical area. An access window or cut out opening is formed adjacent the distal end of the device and is adopted to receive a balloon catheter whereby inflation of the balloon catheter causes it to expand through the access window and drive tissue away from the window or an endoscope or arthroscope. The device discloses a blunt, closed distal tip useful for dissection of surrounding tissue during emplacement of the instrument in the tissue. If desired for certain surgeries, the distal tip can be opened A flattened, ergonomically shaped handle with a throughgoing bore axially aligned with the tubular instrument is mounted at the proximal end over the tubular instrument to facilitate precise control of the device while in use. The handle is semi-circular in cross section with a flat top defining a finger recess. In an alternative embodiment, the handle is removable and one-half of one inch of the surface of the proximal end of the generally tubular portion of the device is knurled, thereby ensuring precise control is maintained whether the handle is used or detached.

The device can be manufactured from stainless steel, cobalt chrome, titanium, nitinol, other metals, polymers, ceramics, composites or other biocompatible materials, and can be manufactured in various sizes and dimensions. It can be made of solid, malleable or flexible material. It can be manufactured by machining, molding or 3D printed.

The multi-functional, grooved director 20 is preferably constructed from surgical steel or polymer material. It is constructed with a tubular member 30 with an integral side guide rail 40 and an ergonomically shaped handle 50 mounted at its proximal end.

The tubular member 30 is cannulated, having a throughgoing, generally cylindrical lumen 31 extending throughout the length of the proximal section and leading an open cut away area 32 on the distal section. A generally blunt, curved closed tip 34 is formed on the distal end of tubular member 30. The tip 34 can alternatively be open or have a solid or optically clean tip that can be fixed or removable from the distal end of the tubular member.

An integral guide rail 40 extends outward from the tubular member 30. An outer rail 42 together with the outer surface 43 of the tubular member forms a straight groove 44 with open ends having a width which is slightly greater than the width of a surgical knife 100 which is used in the invention. The groove 44 preferably has a planar base 45 which keeps the knife 100 aligned and directed as it is slid along groove 44.

The handle 50 of the device is preferably formed from a polymer material and is ergonomically shaped to facilitate handling of the instrument 20. In a preferred embodiment, the handle 50 is generally planar on its top surface 52 and defines a recessed concave surface 54 which accommodates the surgeon's thumb to ensure positive control of the grasped device. A throughgoing lumen (not shown) extends through the handle 50 and is axially aligned with and in communication with the lumen 31 of the tubular member 30. The handle 50 has a semi-circular cross section and a round convex front surface 51. The handle 50 is permanently affixed to the tubular member 30 via an adhesive or sonic welding. If desired both the handle and tube can be formed from a single piece of material such as stainless steel or rigid medically approved plastic material, as for example polyethylene or polypropylene. The cross sections of the proximal end of the tubular member 30 and the handle lumen ensure that when mated, the handle 50 and tubular element 30 are fixed and cannot rotate relative to one another.

The knife 100 is mounted in the groove 44 for slidable entry into the surgical site. The surgical knife 100 has a body 101 which is angled from about 130° to about 150° preferably 140° as shown in FIG. 8 through FIG. 10 by angle A from the blade arm 103. The distal end of the knife has a curved end 102 and a recessed curved cutting blade 104.

The instrument can be reused or disposable. It can be sterilized and is autoclavable and it can be opaque or radiolucent. Furthermore, the device is biologically inert and can serve as a guide for rigid or flexible endoscopes. Thus, it can be seen that it serves as a grooved director for surgical instruments including probes, cannulas, elevators, expanders, cutting blades, lasers, ultrasonic devices, radio frequency devise, mechanical instruments, biological delivery devices, chemical delivery devices and pharmaceutical agents and medicine delivering devices.

A balloon catheter 60 can be mounted through the handle lumen across the floor of the open cut away area 32 against rear wall 35 or is secured against the rear wall 35 of the interior surface of the closed tip 34. The tubular member 30 is cut so that a portion of its wall is removed adjacent its distal end to form an open area or access window 32 allowing the balloon portion 62 of the balloon catheter 60 to expand or the distal end of an arthroscope or endoscope to be exposed to the tissue to undertake the desired surgical procedure. The balloon catheter is seated on the floor of the access window 32 with the balloon 62 facing outward so that expansion of the balloon 62 will elevate the tissue. The proximal tube section of the tubular member 30 extends into the handle 50 or is sonically welded, screwed or glued or securely fixed to the handle 50 by a friction fit and provides anti-roll characteristics to the tubular member 30. An integral side rail can be formed as a right side rail 40 and a left side rail 40(a). The right integral side member 40 is shown in FIGS. 1 through 4 while the left integral side member 40(a) is shown in FIGS. 5 and 6. The access window 32 is defined by the radiused proximal and distal end sections.

FIG. 1 schematically and perspectively depicts the balloon catheter 60 mounted in the lumen of the handle and the axially aligned tubular member lumen 31. The inflation fitting can be a common luer lock style fitting, as is known in the prior art but any fitting suitable for sealably connecting the balloon catheter 60 to the pressurization source 70. The catheter is pressurized by a pump which can be a syringe.

As previously noted, a visualization lens can be used in lieu of the closed tip 34 in an alternative embodiment. A lens can be used at the end of the tubular member. The lens is generally optically transparent so that the expensive optics of an arthroscope or endoscope inserted into this otherwise inexpensive device will be protected while in use. It is contemplated that the visualization lens may be ground with additional refractive indeces as desired, for example, the lens may be ground to provide a magnified view of tissues viewed therethrough. The expander 20 may also be used without first withdrawing the arthroscope or endoscope prior to inflation of the balloon catheter 60.

The present invention can alternatively be provided with a removable handle 50. The handle 50 is frictionally mounted to the proximal tube section of tubular member 30 and may be detached as desired. The proximal tube section of the tubular member 30 can include knurling to ensure positive handling of the tubular element 30 when the handle 50 is not attached and to increase friction and positive attachment of the handle.

In a preferred use, as for example, carpal tunnel treatment; an incision is first cut through the skin and subcutaneous tissue at the base of the palm by sharp dissection. The grooved director 20 is then used to elevate or expand tissues by inserting its blunt tip 34 through the dissection into the hand tissue which ensures dissection of any necessary tissues away from the surgical field without damage. Once emplaced, a pressurization source 70 preferably a syringe filled with fluid such as saline is attached to inflation fitting thereby permitting inflation of balloon 62 and expansion of tissues at the surgical site as desired. The balloon 62 is inflated and deflated to move the muscles away from the nerve and the knife 100 is inserted along groove 44 and its planar floor 45 of the integral side member 40, 40(*a*) to cut the tissue as needed. The device may be used for this operation and for other surgical operations currently performed as known to those skilled in the art, with and without additional support.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

What is claimed is:

1. A surgical director assembly with at least one integral side rail comprising:
    an elongated tubular member with at least one integral side rail secured to said tubular member, said side rail being positioned outside of said tubular member and extending along a portion of said tubular member, said side rail being open at its proximal end and closed at its distal end and defining a straight groove running parallel to the axis of said tubular member, said groove being dimensioned to receive a surgical knife allowing said surgical knife to be slideably mounted in said groove, said tubular member having a distal end portion with a closed rounded tip and defining a throughgoing lumen leading into a cutaway portion dimensioned to receive a second surgical instrument and a handle defining means to secure the proximal end portion of said tubular member.

2. A surgical director assembly with at least one integral side rail as claimed in claim 1 wherein said tubular member and integral side rail is constructed of plastic and is disposable.

3. A surgical director assembly with at least one integral side rail as claimed in claim 1 wherein said tubular member and integral side rail is constructed of metal and is sterilizable.

4. A surgical director assembly with at least one integral side rail as claimed in claim 1 wherein said surgical knife has a base section and a linear arm extending angularly from said base section in a range from about 130° to about 150°, said linear arm defining a blade at its end and being dimensioned to smoothly slide in said side rail groove.

5. A surgical director assembly with at least one integral side rail as claimed in claim 4 wherein said angle is about 140°.

6. A surgical director assembly with at least one integral side rail as claimed in claim 1 wherein said at least one side rail is positioned on the right side of said tubular member.

7. A surgical director assembly with at least one integral side rail as claimed in claim 1 wherein said at least one side rail is positioned on the left side of said tubular member.

8. A surgical director assembly with at least one integral side rail as claimed in claim 1 wherein said tubular member with at least one integral side rail is rigid.

9. A surgical director assembly with at least one integral side rail as claimed in claim 1 wherein said tubular member with at least one integral side rail is flexible.

10. A surgical director assembly with at least one integral side rail as claimed in claim 1 wherein said cut away portion is dimensioned to receive and accommodate a distal end of a balloon catheter and further wherein distal axial movement of said balloon catheter relative to said tubular member is limited by engagement of the balloon catheter distal end with said closed tip of said tubular member, forming a stop.

11. A surgical director assembly with at least one integral side rail as claimed in claim 1 wherein said elongated tubular member has a closed rounded tip which is clear and forms a visualization lens.

12. A surgical director assembly with at least one integral side rail comprising:
    an elongated rigid tubular member with at least one integral side rail secured to said tubular member and a handle mounted to said tubular member, said side rail being positioned parallel to said tubular member and ending in a middle area of said tubular member, said side rail defining a straight linear groove with a planar base, said tubular member having a distal end portion with a closed tip and defining a throughgoing lumen adjacent said linear groove extending into a cutaway portion dimensioned to permit entry of a surgical instrument to engage tissue and perform the desired function of the instrument, said side rail linear groove ending at said tubular member closed tip distal end portion and being open at its opposite end outside of said tubular member, and a surgical knife having a linear base section and a linear arm extending angularly from said base section, said linear arm defining a blade at its distal end and said base section being dimensioned to slide in said side rail groove.

13. A surgical director assembly as claimed in claim 12 wherein said surgical instrument is taken from a group consisting of a balloon catheter, an endoscope, and an arthroscope.

14. A surgical director assembly as claimed in claim 12 wherein said handle defines a central throughgoing bore adapted to fit over the proximal end of said tubular member and defines a planar top surface with at least one finger recess.

15. A surgical director assembly with at least one integral side rail comprising:
    an elongated rigid tubular member with at least one integral side rail positioned adjacent to said tubular member on a side of said tubular member and running parallel to said tubular member, said side rail defining a straight open groove and being dimensioned to be inserted through tissue, said side rail groove being closed at its distal end with said groove being open at its proximal end outside the diameter of said tubular member, said tubular member having a distal end portion with a closed tip and defining a throughgoing lumen extending into a cutaway portion dimensioned to permit expansion of a balloon assembly to engage and dilate tissue and a handle defining tubular member gripping means to hold a proximal end of said tubular member and a surgical knife having a base section and a linear arm extending angularly from said base section, said linear arm defining a blade at its end and said base section being dimensioned to smoothly slide in said side rail groove, and a balloon catheter moveably mounted in said tubular member until said balloon catheter engages the closed tip of said tubular member with pump means fluidly connected to said balloon catheter.

16. A surgical director assembly with at least one integral side rail as claimed in claim 15 wherein said at least one side rail is secured to and positioned on the right side of said tubular member when said tubular member is inserted into tissue.

17. A surgical director assembly with at least one integral side rail as claimed in claim 15 wherein said at least one side rail is secured to and positioned on the left side of said tubular member when said tubular member is inserted into tissue.

* * * * *